United States Patent
Prestipino

(10) Patent No.: US 11,628,049 B2
(45) Date of Patent: *Apr. 18, 2023

(54) APPARATUSES AND METHODS FOR MAKING A FINAL HYBRID PROSTHESIS TO BE ATTACHED TO DENTAL IMPLANTS

(71) Applicant: Anthony James Prestipino, Dunkirk, MD (US)

(72) Inventor: Anthony James Prestipino, Dunkirk, MD (US)

(73) Assignee: Anthony James Prestipino, Dunkirk, MD (US)

( * ) Notice: Subject to any disclaimer, the term of this patent is extended or adjusted under 35 U.S.C. 154(b) by 624 days.

This patent is subject to a terminal disclaimer.

(21) Appl. No.: 16/811,512

(22) Filed: Mar. 6, 2020

(65) Prior Publication Data

US 2020/0205948 A1 Jul. 2, 2020

Related U.S. Application Data

(62) Division of application No. 15/633,251, filed on Jun. 26, 2017, now abandoned, which is a division of application No. 14/174,985, filed on Feb. 7, 2014, now Pat. No. 9,687,327.

(60) Provisional application No. 61/784,908, filed on Mar. 14, 2013.

(51) Int. Cl.
| | |
|---|---|
| *A61C 13/34* | (2006.01) |
| *A61C 8/00* | (2006.01) |
| *A61C 9/00* | (2006.01) |
| *A61C 13/107* | (2006.01) |
| *A61C 13/00* | (2006.01) |
| *G16H 20/40* | (2018.01) |

(52) U.S. Cl.
CPC ............ *A61C 13/34* (2013.01); *A61C 8/0048* (2013.01); *A61C 8/0054* (2013.01); *A61C 8/0098* (2013.01); *A61C 9/0053* (2013.01); *A61C 13/0001* (2013.01); *A61C 13/0004* (2013.01); *G16H 20/40* (2018.01)

(58) Field of Classification Search
CPC . A61C 13/34; A61C 13/0001; A61C 13/0004; A61C 8/0048; A61C 8/0054; A61C 8/0098; A61C 9/0053; G16H 20/40
See application file for complete search history.

(56) References Cited

U.S. PATENT DOCUMENTS 3,464,111 A * 9/1969 Gillard ............... A61C 13/0003
433/171
5,607,628 A * 3/1997 Palazzolo .......... A61C 13/0001
264/222

(Continued)

*Primary Examiner* — Nicholas D Lucchesi
*Assistant Examiner* — Hao D Mai
(74) *Attorney, Agent, or Firm* — Parker Poe Adams & Bernstein LLP

(57) ABSTRACT

The present invention includes apparatuses and methods for making a final hybrid prosthesis to be attached to one or more dental implants. One preferred method includes the step of making a temporary hybrid prosthesis and at about the same time also making a duplicate temporary hybrid prosthesis. The duplicate temporary hybrid prosthesis permits the final hybrid prosthesis to be made with fewer visits to a restorative dentist and with less dental laboratory time than is currently needed when making a final hybrid prosthesis.

16 Claims, 9 Drawing Sheets

(56) References Cited

U.S. PATENT DOCUMENTS

| | | | | |
|---|---|---|---|---|
| 5,711,668 A * | 1/1998 | Huestis | A61C 13/0003 | 433/167 |
| 6,224,375 B1 * | 5/2001 | Diasti | A61C 13/0003 | 433/167 |
| 6,270,701 B1 * | 8/2001 | Kuroda | A61C 13/04 | 264/318 |
| 6,305,939 B1 * | 10/2001 | Dawood | A61C 8/0001 | 433/214 |
| 6,558,162 B1 * | 5/2003 | Porter | A61C 8/0001 | 433/213 |
| 6,730,246 B2 * | 5/2004 | Price | A61C 13/04 | 425/176 |
| 6,790,040 B2 * | 9/2004 | Amber | A61C 8/0001 | 433/213 |
| 7,661,956 B2 * | 2/2010 | Powell | A61C 13/0004 | 433/172 |
| 7,670,516 B2 * | 3/2010 | Rusler | A61C 13/01 | 264/16 |
| 7,758,346 B1 * | 7/2010 | Letcher | A61C 13/0003 | 433/172 |
| 8,011,927 B2 * | 9/2011 | Berckmans, III | A61C 9/0006 | 433/215 |
| 8,185,224 B2 * | 5/2012 | Powell | G06F 30/00 | 700/95 |
| 8,257,083 B2 * | 9/2012 | Berckmans, III | A61C 8/0001 | 433/213 |
| 8,651,858 B2 * | 2/2014 | Berckmans, III | A61C 9/0053 | 433/24 |
| 2002/0090592 A1 * | 7/2002 | Riley | A61C 8/0048 | 433/173 |
| 2003/0108845 A1 * | 6/2003 | Giovannone | A61C 13/2656 | 623/901 |
| 2006/0040236 A1 * | 2/2006 | Schmitt | A61C 11/00 | 433/213 |
| 2007/0281279 A1 * | 12/2007 | Chander | A61C 8/0001 | 433/173 |
| 2009/0081618 A1 * | 3/2009 | LaMar | A61C 8/0048 | 433/218 |
| 2009/0130630 A1 * | 5/2009 | Suttin | A61C 8/009 | 433/174 |
| 2009/0325125 A1 * | 12/2009 | DiAngelo | A61C 8/0048 | 433/199.1 |
| 2010/0183998 A1 * | 7/2010 | Poirier | A61C 1/084 | 433/173 |
| 2012/0046914 A1 * | 2/2012 | Gao | A61C 1/084 | 703/1 |
| 2012/0088208 A1 * | 4/2012 | Schulter | A61C 13/0004 | 700/98 |
| 2012/0179281 A1 * | 7/2012 | Steingart | A61C 13/10 | 703/11 |
| 2012/0276502 A1 * | 11/2012 | Marshall | A61C 9/0053 | 433/199.1 |
| 2013/0071811 A1 * | 3/2013 | Groscurth | A61C 8/0089 | 433/75 |
| 2014/0308624 A1 * | 10/2014 | Lee | A61C 13/0004 | 433/214 |
| 2015/0182314 A1 * | 7/2015 | Morales | A61C 13/0004 | 700/98 |
| 2015/0182316 A1 * | 7/2015 | Morales | A61C 13/01 | 433/199.1 |
| 2016/0135931 A1 * | 5/2016 | Morales | A61C 13/0013 | 433/213 |
| 2016/0199160 A1 * | 7/2016 | Cascione | A61C 8/0095 | 433/199.1 |

* cited by examiner

APPARATUSES AND METHODS FOR MAKING A FINAL HYBRID PROSTHESIS TO BE ATTACHED TO DENTAL IMPLANTS

CROSS REFERENCE TO RELATED APPLICATIONS

This application is a divisional of (and claims the benefit of) pending U.S. patent application Ser. No. 15/633,251, filed Jun. 26, 2017, which is a divisional of (and claims the benefit of) U.S. patent application Ser. No. 14/174,985, filed Feb. 7, 2014, now U.S. Pat. No. 9,687,327 B2, issued Jun. 27, 2017, which claims the benefit of U.S. Provisional Application Ser. No. 61/784,908, filed Mar. 14, 2013, the disclosures of which are hereby incorporated herein by reference in their entirety.

FIELD OF THE INVENTION

The present invention pertains to the field of dental implants.

BACKGROUND OF THE INVENTION

Dental implants are implanted into the jawbone of a patient that has lost some or all of his or her teeth in that jawbone. Various procedures exist for fabricating teeth to be attached to those implants. One procedure currently used is known as the "immediate load protocol." In the immediate load protocol as currently carried out, a patient receives a "temporary hybrid prosthesis" (also referred to as "temporary hybrid") including temporary teeth during the surgical visit during which dental implants are implanted into the jawbone by an implant surgeon. The temporary hybrid includes temporary teeth and metal temporary cylinders. Screws are used to attach the temporary hybrid to the implants. These screws go through bores in the temporary cylinders and screw into threads in the implants. However, the metal cylinders are not connected to one another with metal, but rather are connected to one another with less sturdy acrylic material that is typically used to hold a denture (which includes a set of artificial teeth for one jaw) together. The procedure for making a temporary hybrid under the immediate load protocol as currently carried out is described in detail in the section below entitled "Procedure for Making a Temporary Hybrid Prosthesis to Be Installed in a Patient's Mouth."

After having dental implants implanted, it typically takes several months for the implants to fuse to the patient's jawbone, a process known as "osseointegration." During this time, the tissue in the patient's mouth heals, and the post-surgical swelling goes down. At that point, a patient is ready to have a "final hybrid prosthesis" (also known as a "final hybrid") of teeth made and installed in his or her mouth. This final hybrid differs from the temporary hybrid primarily in that the metal cylinders in the hybrid are attached to one another with a metal bar, such that the cylinders and the bar form one extremely sturdy, integral piece. The final hybrid replaces the temporary hybrid and is intended to more or less be permanently installed in the patient's mouth.

In the immediate load protocol as currently carried out, it takes at least five (and usually more) visits to a restorative dentist (after the surgical visit in which the implant surgeon implants the dental implants in the patient's mouth) to fabricate the final hybrid and have it installed in the patient's mouth. These five or more visits to a restorative dentist typically occur over a period of several months. A significant amount of dental laboratory time occurs between these visits, where the final hybrid is designed, fabricated and perfected based on information obtained during the visits to the restorative dentist. For this reason (and also due to patient and dentist availability), the five or more visits to a restorative dentist must be scheduled over a period of several months. The work done during each of these visits to the restorative dentist, as well as the work done by the dental laboratory between the visits, is described in detail in the section below entitled "Manufacture of Final Hybrid Without Duplicate Temporary Hybrid."

Having to visit a restorative dentist five or more times over several months to have the final hybrid fabricated and installed is inconvenient and expensive to patients, many of whom do not have insurance to help with the costs of dental implants. Moreover, patients who have a temporary hybrid in their mouths are limited in what they are able to eat because the temporary hybrid is not as sturdy as the final hybrid, and thus patients are eager to get the final hybrid installed as quickly as possible. Thus, there is a need for methods that would allow for the final hybrid to be fabricated and installed that require fewer visits to a restorative dentist and could be done in less time, and a need for apparatuses to be used in those methods.

Even when an immediate load protocol is not used, there is still a need for methods by which a final hybrid prosthesis can be made with fewer visits to a restorative dentist and in a shorter period of time, and a need for apparatuses for use in those methods.

SUMMARY OF THE INVENTION

The present invention addresses the drawbacks of current protocols for fabricating a final hybrid prosthesis by permitting such a prosthesis to be fabricated and installed in fewer visits to a restorative dentist, over a shorter period of time, and with less dental laboratory time. For example, the present invention addresses the drawbacks of the immediate load protocol as currently carried out by allowing a final hybrid to be fabricated and installed with just two visits to a restorative dentist (instead of five or more visits), and over a period of just a few weeks. The amount of dental laboratory time needed to design, fabricate and perfect the final hybrid is also significantly reduced.

In accordance with one aspect of the present invention, this is accomplished by the fabrication of a "duplicate temporary hybrid prosthesis" (also known as a "duplicate temporary hybrid") at the same time that the first temporary hybrid is fabricated and installed in the patient's mouth, which is during the surgical visit during which the dental implants are implanted into the patient's jawbone in the immediate load protocol as currently carried out. This duplicate temporary hybrid may be fabricated during time when the patient would otherwise still be recovering at the place of the surgery, and thus does not add any appreciable amount of time to the length of the surgical visit when the dental implants are implanted in the patient's mouth.

In accordance with another aspect of the present invention, the duplicate temporary hybrid is used to simplify and shorten the process of making the final hybrid. Whereas five or more visits to a restorative dentist over a period of several months are required to fabricate and install a final hybrid under the immediate load protocol as currently carried out, only two visits to a restorative dentist over a period of just a few weeks are required when the duplicate temporary hybrid according to the present invention is utilized.

According to some implementations of the present disclosure, a method of making a final hybrid prosthesis to be attached to one or more dental implants in a patient's mouth includes making a temporary hybrid prosthesis to be attached to one or more dental implants in a patient's mouth. A duplicate temporary hybrid prosthesis is made. The duplicate temporary hybrid prosthesis is used in making the final hybrid prosthesis.

According to some implementations of the present disclosure, a duplicate temporary hybrid prosthesis for use in making a final hybrid prosthesis includes a unitary structure in the shape of teeth and gum portions of a temporary hybrid prosthesis to be attached to dental implants in a patient's mouth. The unitary structure is made entirely of one type of material.

According to some implementations of the present disclosure, a method of making a final hybrid prosthesis to be attached to a plurality of dental implants in a patient's mouth includes making a temporary hybrid prosthesis to be attached to the plurality of dental implants in the patient's mouth. By use of the temporary hybrid prosthesis, a stone model of the patient's mouth is developed. By use of the stone model, a duplicate temporary hybrid prosthesis is developed. After soft tissue adjacent to the plurality of dental implants has healed, the duplicate temporary hybrid prosthesis is attached to the plurality of dental implants. While the duplicate temporary hybrid prosthesis is attached to the dental implants, impression material is used to identify the contours of the healed soft tissue. An updated stone model is created with the healed soft-tissue contours identified by the impression material. The final hybrid prosthesis is made by use of the updated stone model and the duplicate temporary hybrid prosthesis.

BRIEF DESCRIPTION OF THE DRAWINGS

Specific examples have been chosen for purposes of illustration and description, and are shown in the accompanying drawings, forming a part of the specification.

DETAILED DESCRIPTION

Figure 1:
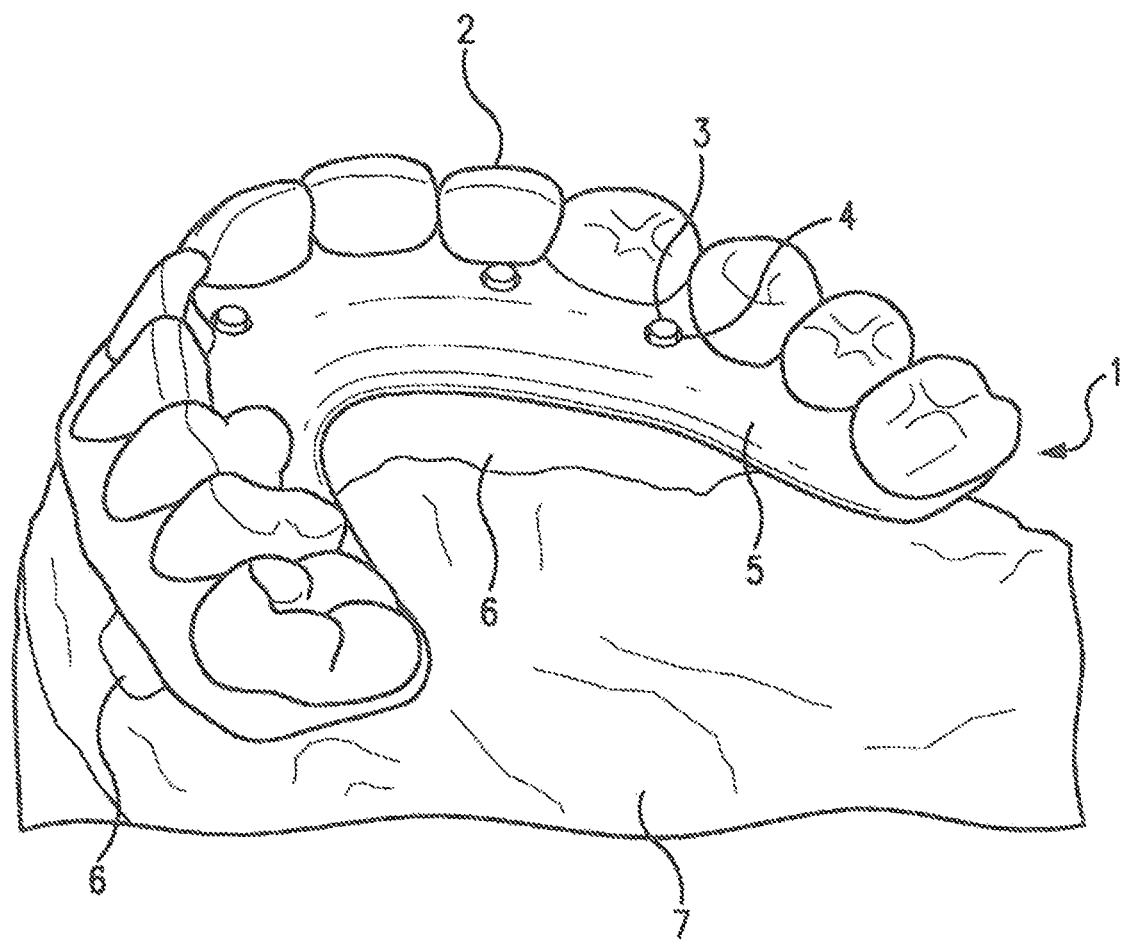
FIG. 1 illustrates a temporary hybrid prosthesis to be installed in the patient's mouth on a working model of one of the patient's jawbones.

Procedure for Making Temporary Hybrid Prosthesis to be Installed in Patient's Mouth The typical procedure for making a temporary hybrid prosthesis to be installed in the patient's mouth under the immediate load protocol as currently carried out proceeds in the following manner. Several weeks before the surgical visit where the patient is to have dental implants implanted by an implant surgeon, a restorative dentist takes impressions of the patient's upper and lower teeth using techniques familiar to those skilled in the art. The dentist also measures the vertical dimension of occlusion ("VDO") of the patient's jaws, and takes a "bite," which is an impression of the interface between the patient's upper and lower teeth. These impressions, the VDO information and this bite are used by a dental laboratory to build a working model of the patient's upper and lower jaws with teeth. The model may then be used to make a "lab bite," which is an impression of the interface between the upper and lower teeth in the model.

The impression of the teeth to be replaced is also used by the dental laboratory to make a temporary denture that will be used in making the temporary hybrid. The temporary denture does not have any metal cylinders in it, nor does it have any holes in it to facilitate attachment to the implants. The teeth in the temporary denture are denture teeth (or hybrid teeth, which are stronger) that are typically held together with pink acrylic material (which forms the "gums" of the denture). The temporary denture is typically the shape of a horseshoe with the middle part of the horseshoe filled in (i.e., the shape of half of an oval).

During the surgical visit where dental implants are implanted by the implant surgeon, impression material is placed onto the temporary denture on the side facing the implants, and the temporary denture is placed into the patient's mouth. This impression material records the precise location and orientation of the implants. Using the index created by the impression material, holes are cut in the temporary denture that match up with the location of the implants in the patient's mouth. When a patient is having all of his or her teeth on one jawbone replaced, it is typical for five dental implants to be implanted in that jawbone. When, for example, five dental implants are implanted in one jawbone, holes are cut in the temporary denture that match up with the location of the implants in the patient's mouth. Next, temporary metal cylinders are attached to the implants with screws. The holes in the temporary denture are just large enough to allow the temporary metal cylinders to slide through them. After the temporary metal cylinders are attached to the implants with screws, a horseshoe-shaped rubber dam is laid down on top of the patient's gum with holes in it to allow the temporary metal cylinders to fit through the rubber dam. The index that was previously used to ensure that the holes in the temporary denture were made in the proper location may also be used to ensure that the holes in the rubber dam are made in the proper location. This rubber dam protects the patient's gum during the next step.

In this next step, acrylic is applied to the temporary cylinders. Any suitable acrylic may be used. One suitable acrylic is made by mixing Jet acrylic polymer (a powder) with Jet acrylic monomer (a liquid). The rubber dam prevents acrylic from coming in contact with the patient's gums. Next, the temporary denture (with the holes in it that correspond to the locations of the temporary cylinders) is placed into the patient's mouth with the temporary denture contacting the rubber dam and the temporary cylinders protruding through the holes in the temporary denture. The relationship of the two jaws is stabilized using the bite or lab bite previously made. The acrylic is allowed to at least partially dry and harden, which happens very rapidly. The dried acrylic attaches the temporary cylinders to the temporary denture. The screws holding the temporary cylinders onto the implants are removed and the temporary denture—with the temporary cylinders now attached—is removed from the patient's mouth. The rubber dam typically remains attached to the temporary denture when that is removed (because of the acrylic). If that happens, the rubber dam is pulled off of the temporary denture. The temporary denture with the temporary cylinders now affixed to it may then be cured in a pressure pot in warm water (such as at 20 psi for 5 minutes) to make the unit sturdier. The plastic material that connects opposite sides of the horseshoe (i.e., that "fills in" the horseshoe) is then cut away, leaving a horseshoe-shaped temporary hybrid. The flange of the denture that covers the patient's gums is also cut away. This hybrid is then polished up and installed in the patient's mouth. The access holes in the denture for the screws are filled in with rubber plugs so that food does not get stuck into the access holes. These rubber plugs can be removed later to unscrew the screws and thereby remove the temporary hybrid from the patient's mouth.

In this manner, in the immediate load protocol as currently carried out, the process of taking a temporary denture and turning it into a temporary hybrid prosthesis that may be installed in the patient's mouth (as well as the actual installation of the temporary hybrid) occurs during the surgical visit when the dental implants are implanted.

This procedure for making a temporary hybrid prosthesis is generally described in BIOMET 3I, Diem 2 Guidelines, Rev. A (11/11), which is incorporated herein by reference.
Procedure for Making Duplicate Temporary Hybrid Prosthesis As referred to above, the present inventor has discovered that substantial benefits may be obtained if a duplicate temporary hybrid prosthesis is fabricated at the same time that the temporary hybrid to be installed in the patient's mouth is fabricated. This duplicate temporary hybrid is fabricated in the following manner.

After the temporary hybrid to be installed in the patient's mouth is fabricated (as described above), but during the surgical visit when the dental implants are implanted into the patient, "implant analogs" are attached to the temporary cylinders of the temporary hybrid with screws, just as the temporary cylinders would be attached to the implants in the patient's mouth with screws. These implant analogs are meant to perform the same function in a working model of the patient's mouth that the "real" implants perform in the patient's real mouth. A thin layer of soft tissue material—silicone that is intended to mimic the contour and texture of the gums—is then squirted onto the side of the temporary hybrid from which the implant analogs protrude and allowed to dry. Any type of soft tissue material may be used, but one particularly preferred type of soft tissue material is Coltene Gi-Mask #8065 from BENCO. The temporary hybrid with the soft tissue material and analogs attached is then pressed into a patty of fast-setting dental stone (with the teeth protruding away from the dental stone and the analogs protruding toward the dental stone). Any type of dental stone may be used, but one particularly preferred type of dental stone is Mounting Stone White IOS Type 3 #095021202 by WHIP MIX. The stone is allowed to dry and harden, leaving a working model of one half of the patient's jaw with the temporary hybrid attached to it.

FIG. 1 depicts this working model. Temporary hybrid prosthesis 1 includes teeth 2 and gums 5 from the temporary denture. The temporary hybrid prosthesis 1 also includes the holes 4 that were cut into the temporary denture to align with the dental implants in the patient's mouth. In FIG. 1, one can see the tops of the temporary cylinders 3 poking out of the holes 4. In the working model, temporary hybrid prosthesis 1 is mounted on hardened dental stone 7 (which mimics the jawbone), and is separated from the stone by a thin layer of soft tissue material 6, which mimics the patient's gums with which the temporary hybrid prosthesis will interface. Screws go through bores in each of the temporary cylinders 3 and screw into threads on the implant analogs (not shown) embedded in the dental stone, which mimics the dental implants in the patient's mouth.

The temporary hybrid may be removed by unscrewing the screws holding the temporary cylinders to the implant analogs. This leaves hardened dental stone with a thin horseshoe-shaped layer of soft tissue material on the surface of the dental stone, with the implant analogs protruding from the stone and through the horseshoe-shaped soft tissue material. This mimics the half of the patient's jaw to which the temporary hybrid is to be attached.

As mentioned previously, before the surgical visit where the dental implants are implanted, impressions of the patient's upper and lower teeth and a bite are made using techniques familiar to those skilled in the art, and VDO information is collected, and the impressions, bite and VDO information are used to build a working model of the patient's upper and lower jaws with teeth. The upper and lower jaws of the model are placed in relation to one another with an "articulator," which can be used to orient the upper and lower jaws so that they are in the same relationship that they are in the patient's mouth (e.g., with the proper VDO, and with the proper horizontal relationship of the upper and lower jaws, or "centric relation"). Any suitable articulator may be used, such as hinged articulators sold by HARRIS. A pin on the upper jaw is unscrewed to a length so that it just contacts a plate on the lower jaw when the two jaws are closed. This pin is used to make sure that the vertical distance between the upper and lower jaws is consistent with the VDO information previously recorded. The bite made previously is used to ensure that the horizontal relationship between the upper and lower jaws is correct. The articulator has a hinge on it that permits the jaws to be opened just like a human mouth. In this way, the articulator with the representations of the upper and lower jaws included in it provides a good working model of the patient's mouth before the dental implants or the temporary hybrid are installed.

After the temporary hybrid is fabricated, and after that temporary hybrid and dental stone are used to fabricate a new model of the half of the patient's jaw to which the temporary hybrid is to be attached (as described above), the articulator is used to orient this new model of the half of the patient's jaw to which the temporary hybrid is attached with the existing model of the other half of the patient's jaw. One can ensure that the temporary hybrid provides the proper VDO by checking to see that the pin on the representation of the upper jaw just touches the plate on the model of the lower jaw. Similarly, one can ensure that the temporary hybrid provides the proper centric relation by using the bite or lab bite. In this way, the articulator with the representation of each half of the patient's jaw attached to it provides a good working model of the patient's mouth after the temporary hybrid is installed.

To make the duplicate temporary hybrid, the temporary hybrid to be installed in the patient's mouth is attached to the representation of the half of the patient's mouth to which the temporary hybrid will be attached (the dental stone with soft tissue material and implant analogs) with screws that go through the temporary cylinders and screw into the implant analogs. This is depicted in FIG. 1. Next an impression (or matrix) is taken of the temporary hybrid using lab putty in a manner familiar to those skilled in the art. The impression (or matrix) made with lab putty is then removed and set aside. Next the temporary hybrid is removed from the representation of the half of the patient's mouth to which the temporary hybrid will be attached by unscrewing the screws holding the temporary cylinders to the implant analogs. Next, new temporary cylinders are attached with screws to the implant analogs in the model of the patient's mouth. These are cut down to size so that the VDO will be the same in the patient's mouth with the temporary hybrid to be installed in the patient's mouth and the duplicate temporary hybrid. The access holes in the temporary cylinders are blocked. A separator material such as petroleum jelly is applied to the dental stone, soft tissue material and analogs on the model of the patient's jaw to prevent acrylic from sticking to the dental stone, soft tissue material or analogs.

Figure 2:
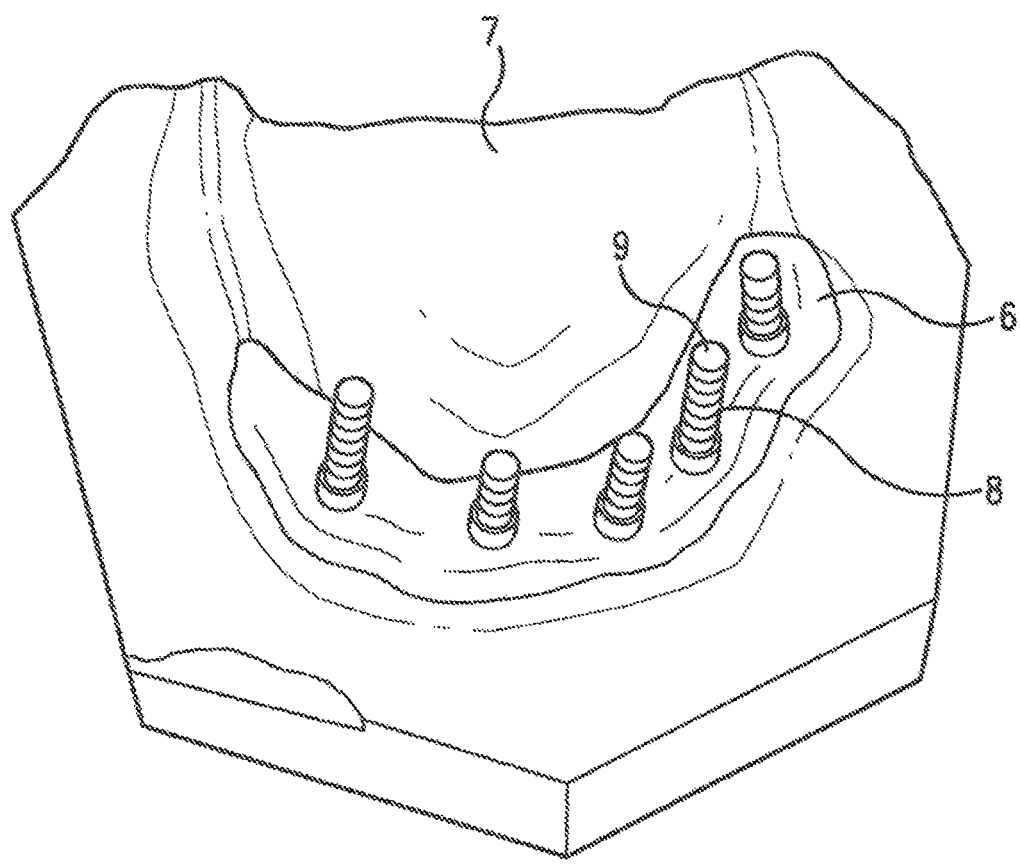
FIG. 2 illustrates soft tissue material and temporary cylinders on a working model of one of the patient's jawbones.

FIG. 2 depicts the model of the patient's jaw with the temporary cylinders 8 to be used in making the duplicate temporary hybrid prosthesis protruding from the hardened dental stone 7 and through the soft tissue material 6. The access holes 9 at the top of the temporary cylinders are blocked.

Figure 3:
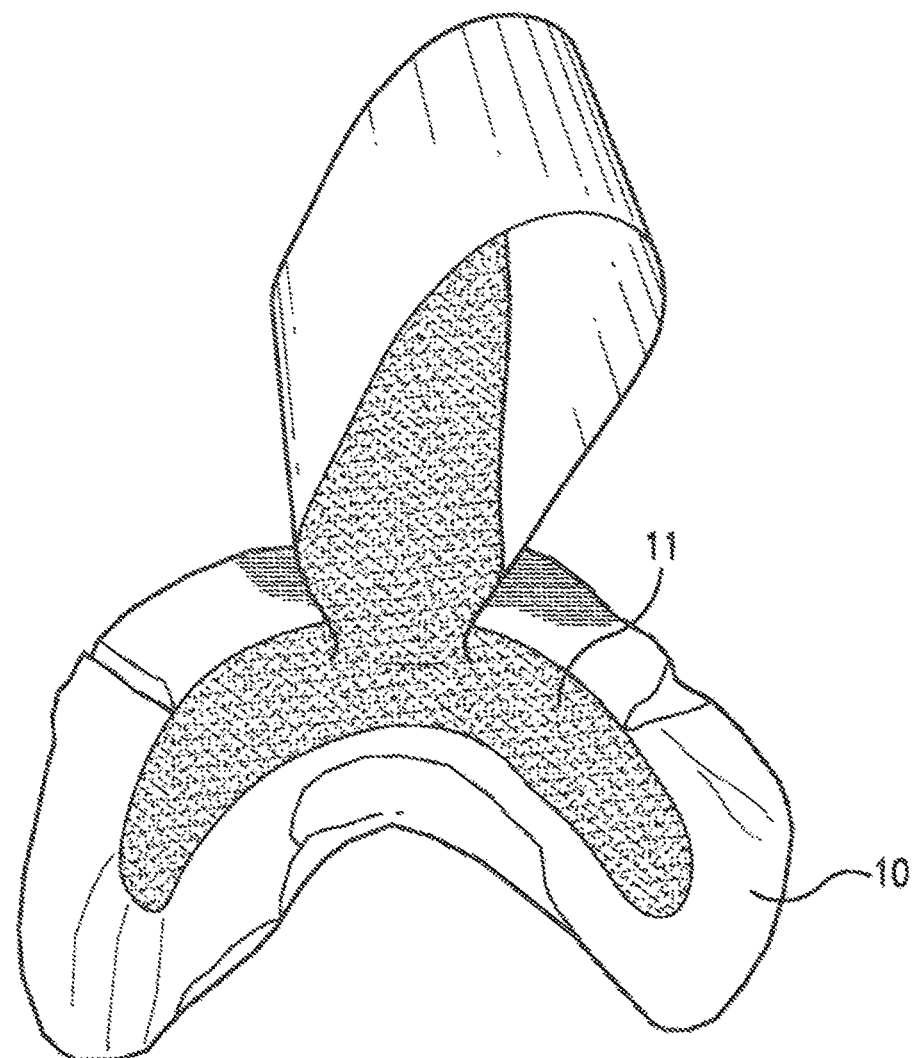
FIG. 3 illustrates acrylic material being poured into an impression (or matrix) of the temporary hybrid prosthesis to be installed in the patient's mouth.

The impression (or matrix) made of lab putty is now filled with soft acrylic. FIG. 3 depicts acrylic 11 being poured into impression (or matrix) 10. This impression (or matrix) is made by pressing the lab putty onto the surface of the temporary hybrid prosthesis 1.

The impression (or matrix) is placed onto the model of the patient's jaw to which the temporary hybrid is to be installed (which is itself attached to the articulator) so that the temporary cylinders are stuck into the soft acrylic. The articulator is closed so that the VDO is correct, and the two jaws are secured to one another in some manner (e.g., with a rubber band). Note that the closing of the articulator may cause the teeth from the jaw that is not being repaired to cut a small hole in the lab putty holding the soft acrylic. For this reason, a separator material (such as petroleum jelly) is placed onto the teeth of the jaw that is not being repaired so that acrylic does not stick to those teeth. The acrylic dries and hardens.

Figure 4:
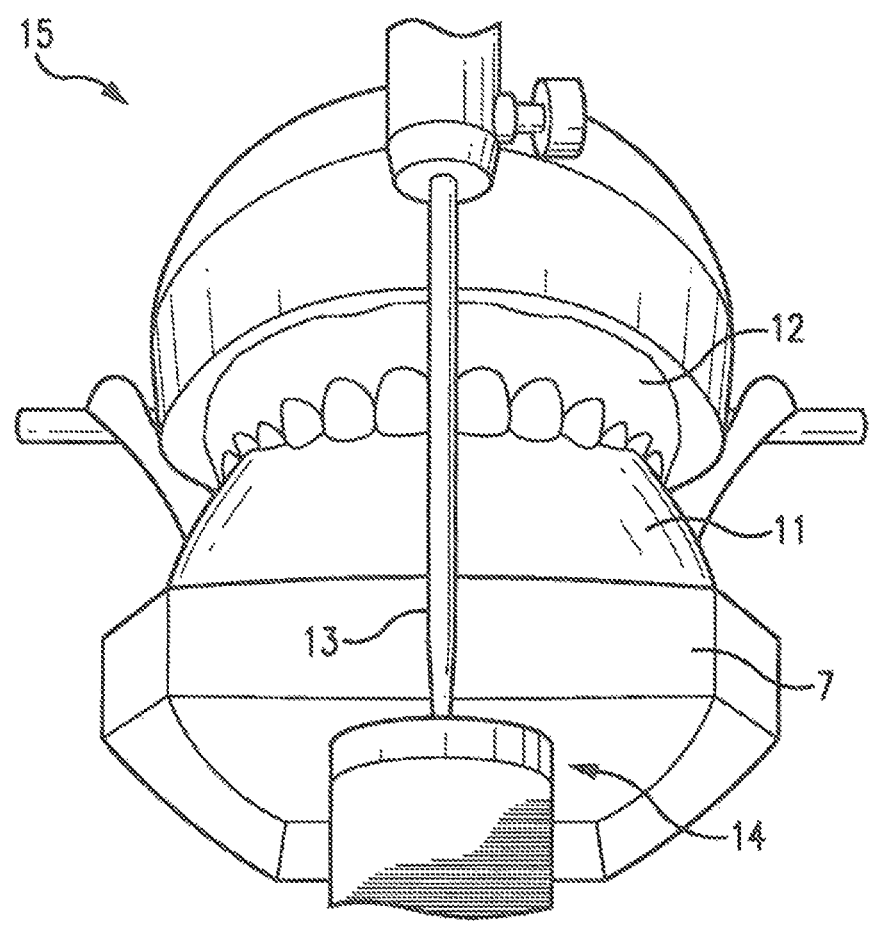
FIG. 4 illustrates an articulator with one jaw being composed of the impression (or matrix) with acrylic material in it on top of a working model of one of the patient's jawbones.

FIG. 4 depicts an articulator 15 that includes a model of the patient's opposing jaw (the jaw that is not being repaired) 12, and the model of the patient's jaw that is being repaired including hardened dental stone 7 and impression (or matrix) 11 with the acrylic that was poured into the impression (or matrix) in FIG. 3 inside of it. A pin 13 is attached to the model of the upper jaw, and a metal plate 14 is attached to the model of the lower jaw. The length of the pin can be adjusted so that the distance between the upper and lower jaws is the same as in the patient's mouth. The VDO for the model is correct when the pin just contacts the metal plate.

The articulator with the acrylic-containing matrix forming one of the two jaws and the model of the other jaw may be placed in a pressure pot to make the acrylic stronger (e.g., at 20 psi for 5 minutes in warm water). The impression or matrix is removed from the hardened acrylic. The temporary cylinders are now firmly embedded in the hardened acrylic. The hardened acrylic with the temporary cylinders embedded in it constitutes the duplicate temporary hybrid.

Figure 5:
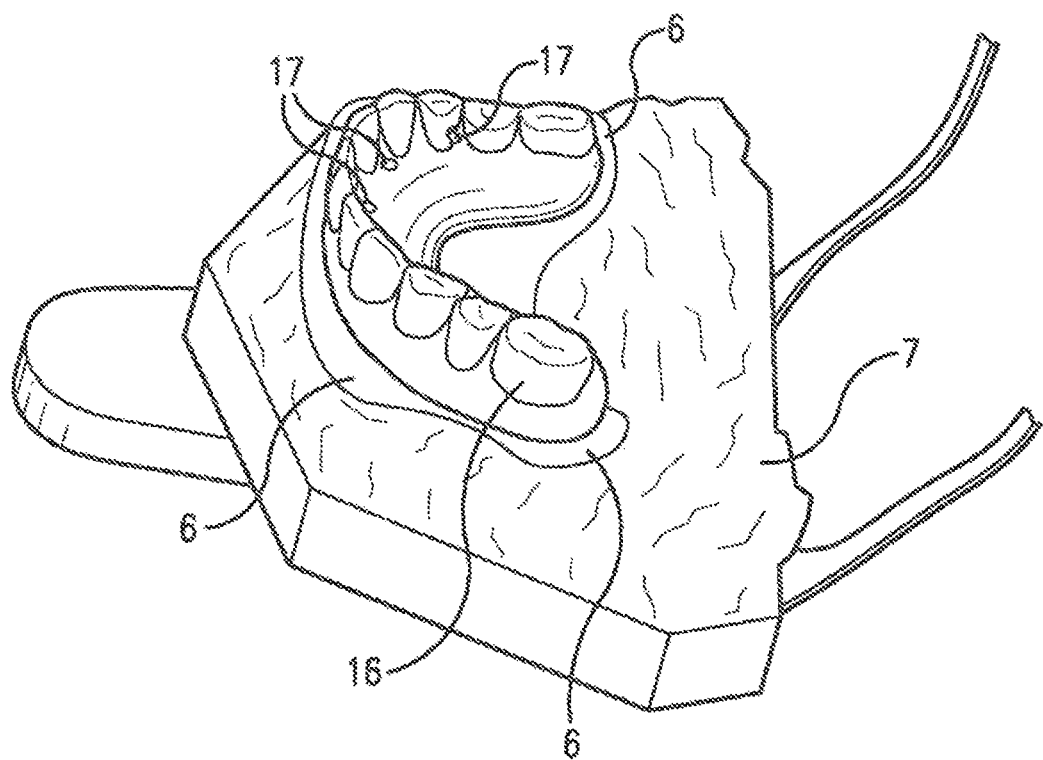
FIG. 5 illustrates a duplicate temporary hybrid prosthesis attached to a working model of one of the patient's jawbones.

FIG. 5 depicts the duplicate temporary hybrid 16 after the impression (or matrix) has been removed. It is attached to the working model of the patient's jaw, which includes hardened dental stone 7 and soft tissue material 6. There are holes 17 in the duplicate temporary hybrid that lead to the temporary cylinders and screws.

The screws holding the temporary cylinders to the implant analogs are accessed by removing the material used to block the access holes in the temporary cylinders and any acrylic needed to be removed, and the screws are unscrewed so that the temporary cylinders may be unfastened from the implant analogs. This leaves a duplicate hybrid made out of acrylic, with temporary cylinders in it at the same locations and in the same orientations as the temporary cylinders in the temporary hybrid to be installed in the patient's mouth.

This duplicate temporary hybrid is then polished up in the same manner as the temporary hybrid to be installed in the patient's mouth. Before the surgical visit where the dental implants are implanted is over, the restorative dentist installs the duplicate temporary hybrid in the patient's mouth to make sure that it fits in the same way as the temporary hybrid to be installed in the patient's mouth. In particular, the restorative dentist makes sure that the placement and orientation of the temporary cylinders on the duplicate temporary hybrid are correct, and that the VDO and centric relation of the temporary hybrid are correct.

In this manner, a duplicate temporary hybrid (with teeth made out of acrylic) may be fabricated during the surgical visit during which dental implants are implanted in the patient. Although referred to herein as a "duplicate" temporary hybrid, this hybrid is actually different from the temporary hybrid to be installed in the patient's mouth in that the teeth and gum portions of the duplicate temporary hybrid are made entirely out of one type of material (e.g., acrylic), whereas in the temporary hybrid to be installed in the patient's mouth, the teeth portions are made out of one type of material (e.g., denture teeth or hybrid teeth) while the gum portions are made out of a different type of material (e.g., pink acrylic). In one embodiment, white acrylic is used to make the duplicate temporary hybrid so that if the duplicate temporary hybrid is ever needed to replace the temporary hybrid to be installed in the patient's mouth (because, for example, the temporary hybrid to be installed in the patient's mouth is damaged), it will appear similar to the duplicate temporary hybrid to be installed in the patient's mouth (i.e., it will have white "teeth").

The temporary cylinders included in the duplicate temporary hybrid may either be the same type of temporary cylinder included into the temporary hybrid to be installed in the patient's mouth, or they may be a different type of temporary cylinder. For example, while the temporary cylinders included in the temporary hybrid to be installed in the patient's mouth must be anodized and approved by regulatory authorities such as the Food and Drug Administration (FDA) to be placed in the patient's mouth for an extended period of time (at least six months), the temporary cylinders included in the duplicate temporary hybrid do not need to be anodized or approved by regulatory authorities to be placed in the patient's mouth for an extended period of time. Accordingly, the temporary cylinders included in the temporary hybrid to be installed in a patient's mouth can be less expensive than the temporary cylinders included in the temporary hybrid to be installed in a patient's mouth.

The fabrication of the duplicate temporary hybrid does not add appreciably to the length of the surgical visit because during the time that the duplicate temporary hybrid is made, the patient is typically recuperating in a post-operative room. The only additional time needed from the patient is the minimal amount of time needed for the duplicate temporary hybrid to be installed to make sure that it fits properly in the patient's mouth. During the surgical visit, it takes less than an hour of dental laboratory time to make the duplicate temporary hybrid.

Use of Duplicate Temporary Hybrid in Making Final Hybrid

As referred to previously, the process of making a final hybrid commences after the implants have become firmly attached to the patient's jawbone (osseointegration), and after patient's gums have healed and stopped swelling. At this point, the duplicate temporary hybrid made during the surgical visit (when the dental implants were implanted) can be used to make a final hybrid with just two patient visits to the restorative dentist.

Since the surgical visit when the dental implants were implanted, the swelling in the patient's gums will have gone down. Thus, a gap between the temporary hybrid that the patient has been wearing and the patient's gums will have developed. There will be an identical gap between the patient's gums and the duplicate temporary hybrid when the latter is installed in the patient's mouth.

During the first visit to the restorative dentist after the surgical visit in which the dental implants were implanted, the temporary hybrid that the patient has been wearing is removed, and the duplicate temporary hybrid is screwed onto the dental implants. The VDO and centric relation with the duplicate temporary hybrid are then checked. Whether the duplicate temporary hybrid fits properly onto the implants is also checked.

The duplicate hybrid is then removed, and adhesive is applied to the surface of the duplicate temporary hybrid that contacts the patient's gums. One appropriate adhesive is Vinyl-Polysiloxane Tray Adhesive. The duplicate temporary hybrid (with the adhesive applied to it) is then screwed onto the implants. Now impression material is squirted into the gaps between the patient's gums and the surface of the duplicate hybrid with adhesive attached to it. The adhesive helps attach the impression material to the duplicate hybrid. One appropriate type of impression material is Vinyl Polysiloxane Impression Material, Regular Set-Light Body-Hydrophilic, ISO 4823 Type 3 (50 ml Base Paste/Catalyst Paste) made by 3M.

Figure 6:
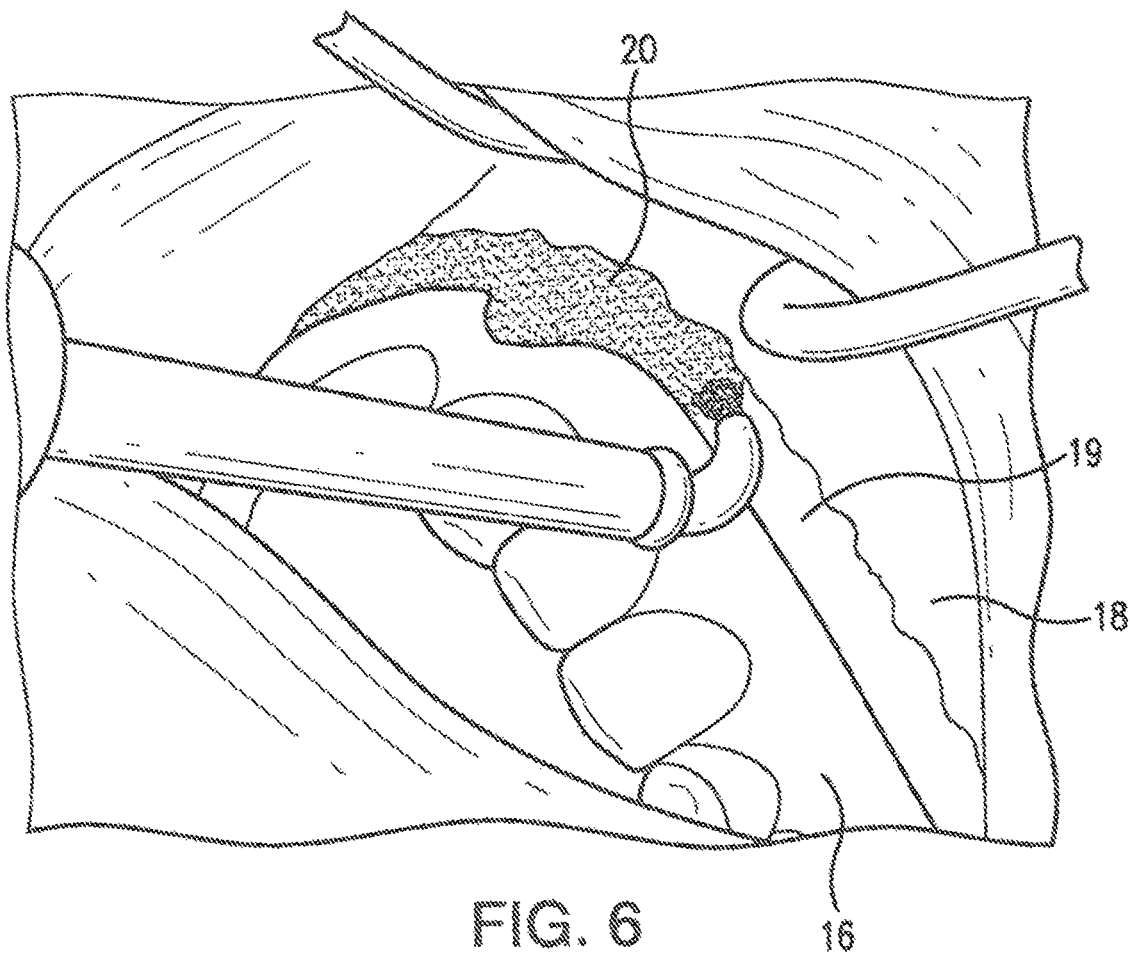
FIG. 6 illustrates the duplicate temporary hybrid prosthesis attached to the dental implants in a patient's mouth, and impression material being squirted into the gap between the duplicate temporary hybrid prosthesis and the patient's healed gums.

FIG. 6 depicts the duplicate temporary hybrid 16 installed in a patient's mouth after osseointegration has occurred and the swelling in the patient's gums has gone down. Because the swelling in the gums has gone down, there is a gap 19 between the duplicate temporary hybrid and the patient's gums 18. Impression material 20 is injected into this gap 19.

The impression material is allowed to harden, and then the duplicate temporary hybrid is removed from the patient's mouth. Note that the hardened impression material provides an impression of the patient's gums (i.e., the healed gums) to which the final hybrid will be attached.

Figure 7:
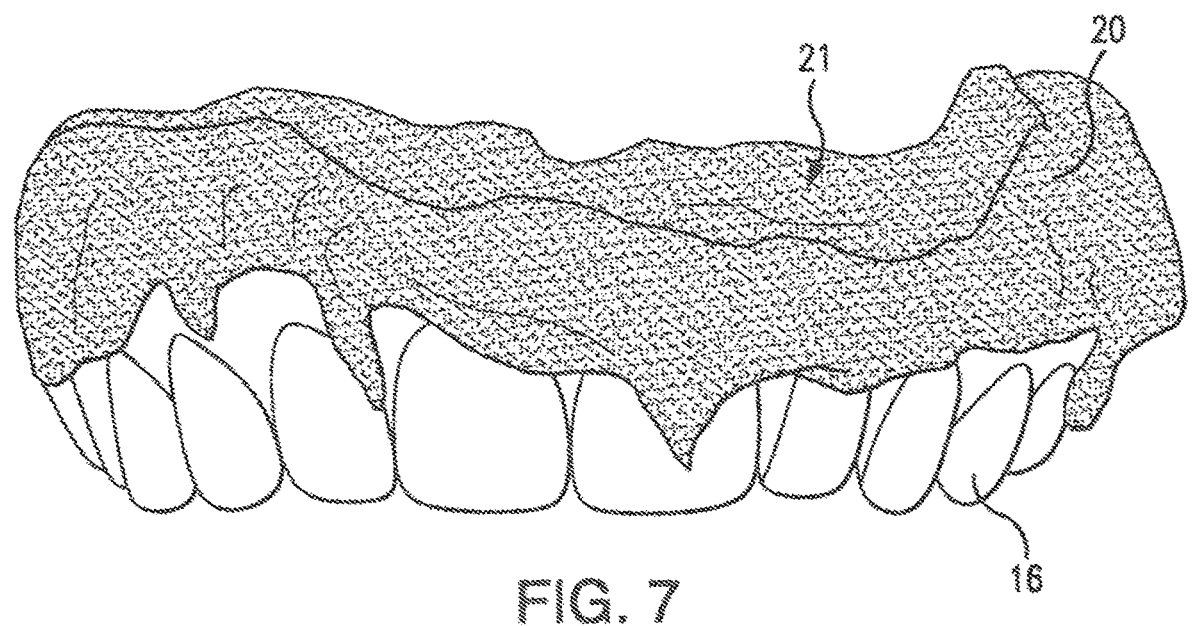
FIG. 7 illustrates the duplicate temporary hybrid prosthesis with the impression material of FIG. 6 on it after it has been removed from the patient's mouth.

FIG. 7 depicts the duplicate temporary hybrid prosthesis 16 after the impression material 20 has hardened and the duplicate temporary hybrid has been removed from the patient's mouth. The top surface 21 of the impression material 20 provides an impression of the contour of the patient's healed gums.

The temporary hybrid that the patient has been wearing is re-installed. This ends the first visit to the restorative dentist.

The duplicate temporary hybrid with the impression material attached to it is then used to update the model of the half of the patient's jaw to which the temporary hybrid is attached in the following manner. At this point, the model consists of hardened dental stone covered by a thin layer of soft tissue material in a horseshoe shape with one end of the implant analogs embedded in the dental stone and the other end protruding through the soft tissue material. This soft tissue material mimics the contour and texture of the patient's gums at the time of the implant procedure, when they were swollen. Since it is no longer necessary to mimic the gums in this swollen state, the soft tissue material is removed from the model. Any excess impression material (i.e., impression material that was not in contact with the patient's gums) is trimmed away. The duplicate temporary hybrid with the impression material attached to it is now screwed onto the model of the half of the patient's jaw to which the temporary hybrid is attached. New soft tissue material is squirted into the void between the dental stone and the trimmed impression material (which contains an impression of the healed gum tissue). The soft tissue material is allowed to harden. When the duplicate temporary hybrid is removed, the soft tissue material stays behind on the dental stone (due to the friction between the soft tissue material on the one hand and the crevices in the stone and implant analogs on the other), leaving a model of the half of the patient's jaw to which the temporary hybrid is attached as it now exists (e.g., with unswollen gums).

Now, a computer scanner is used to make a three-dimensional drawing of the duplicate temporary hybrid attached to a representation of the surface of the patient's mouth to which it will be attached. Any suitable computer scanner may be used. Suitable computer scanners are made by 3 SHAPE. The three-dimensional drawing represents the shape of the final hybrid that will be installed in the patient. A computer-aided design (CAD) program is used to design a sturdy horse-shoe shaped bar that will fit inside the gum portion of the final hybrid and that will include cylinders in locations that match up properly with the dental implants. Any suitable CAD program may be used. Suitable CAD programs are sold by 3 SHAPE. The bar is often made of titanium.

Figure 8:
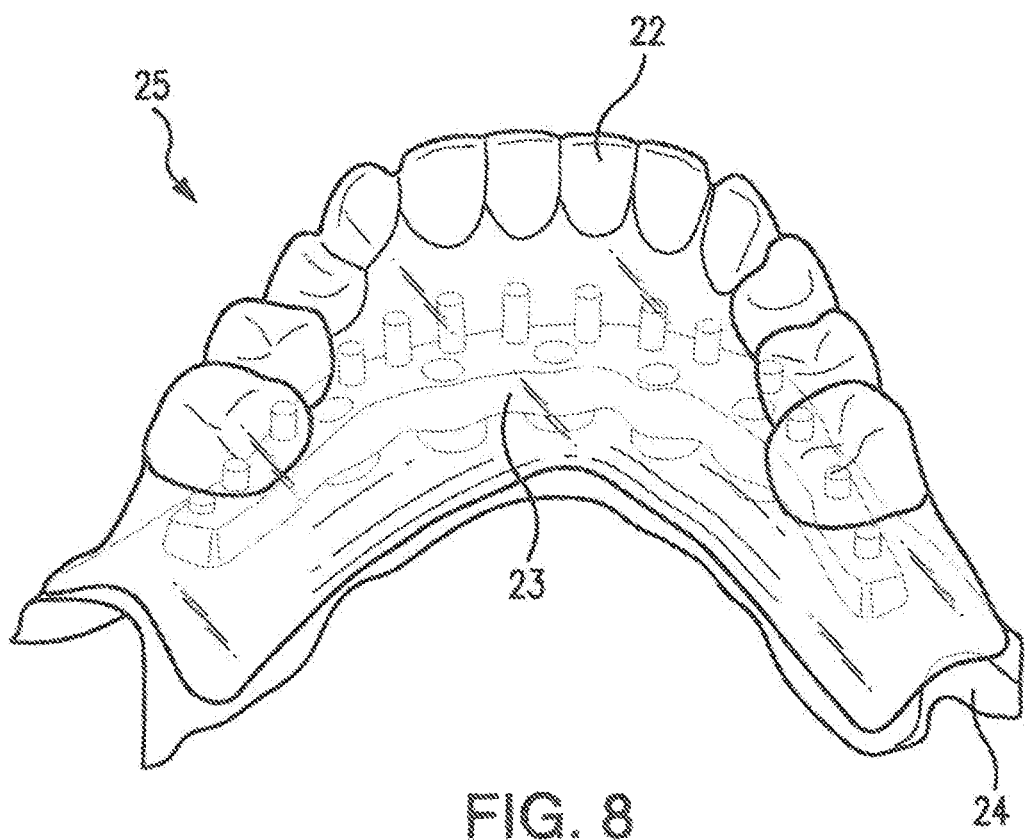
FIG. 8 is a CAD drawing showing the metal bar inside the outline of the final hybrid prosthesis.

FIG. 8 depicts a CAD drawing 25 including a representation 22 of the final hybrid prosthesis and a representation 24 of the surface to which it will be attached in the patient's mouth. The representation 22 of the final hybrid prosthesis is translucent so that a representation of the metal bar 23 can be seen inside of the representation of the final hybrid prosthesis. The cylinders that match up with the dental implants are found on the bottom of the bar. Protrusions on the upper side of the bar help hold the teeth in place.

Once the design of this bar has been determined using the CAD program, an actual bar is made with a milling machine using the design determined on the computer. Such bars will be familiar to those skilled in the art, and are manufactured by companies such as BIOMET 3I.

Once the bar is manufactured, it is checked to make sure it properly fits onto the model of the patient's jaw to which the temporary hybrid is attached by screwing it onto that model by putting screws through the cylinders on the bar and screwing them into the implant analogs on the model. This shows the relationship between the bar and the soft tissue material, which represents the relationship between the bar and the patient's gums.

Next, denture teeth (or hybrid teeth, which are stronger than denture teeth) are attached to the bar using wax using techniques familiar to those skilled in the art. Any suitable type of denture or hybrid teeth may be used. One such type of teeth is Heraeus Mondial® teeth. Any suitable wax may be used, such as pink denture wax. The bar with the teeth attached to it with wax is then screwed onto the model and checked to see whether the VDO and centric relation are correct. At that point, the bar with teeth attached to it with wax is pressed into soft dental stone in a denture flask (or brass bowl). The stone hardens, and the wax is then boiled out. This leaves just the bar and the teeth, but without anything holding the teeth to the bar. The stone in the denture flask holds the bar and the individual teeth in place. A thin layer of pink opaque material that is the color of the patient's gums is spread onto the bar so that the bar is not visible through the acrylic gums when looking at the final hybrid. Such materials are familiar to those skilled in the art, including Tru-Paque® acrylic liquid opaque material. Then soft acrylic (which is the pink color of gums) is put into the denture flask and allowed to harden around the bar and the teeth. The hardened acrylic holds the bar to the teeth and vice versa, and also is designed to look like the patient's natural gums. The bar with the hardened acrylic and teeth constitutes the final hybrid. This final hybrid is polished. It is then attached to the jaw model to make sure that it fits properly and that the VDO and centric relation are correct.

At the second visit with the restorative dentist, the temporary hybrid is removed, and the final hybrid is installed. The holes for the screws are filled in, and the process is complete.

Figure 9:
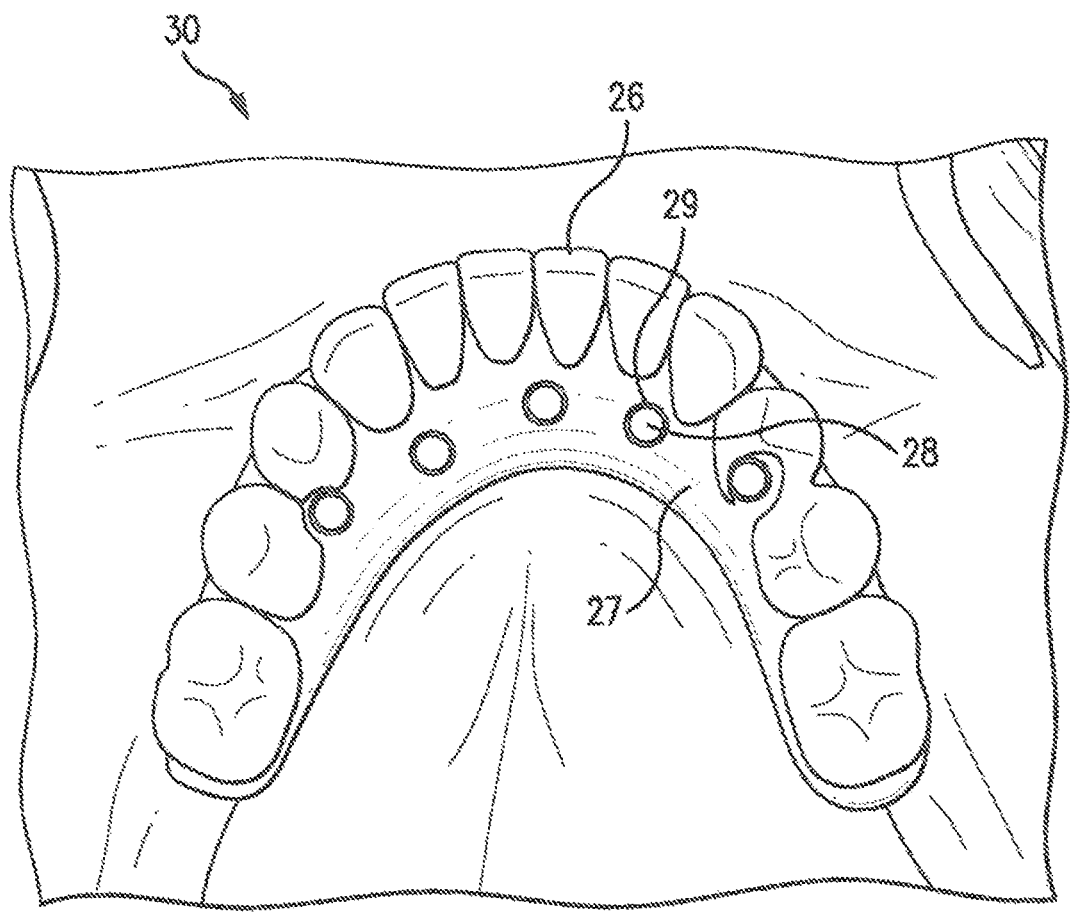
FIG. 9 illustrates the final hybrid prosthesis made according to the present invention after it has been inserted in a patient's mouth.

FIG. 9 depicts a final hybrid prosthesis 30 that has been screwed into a patient's mouth. The final hybrid includes teeth 26 and acrylic gums 27. Holes 29 in the final hybrid allow one to access screws 28 that protrude through the cylinders on the metal bar and attach the final hybrid to the dental implants. These holes are filled in with composite material by the restorative dentist. It should be noted that while the inventive process involving the duplicate temporary hybrid prosthesis of the present invention has been described relative to hybrid bars, the process and the duplicate temporary hybrid prosthesis can also be applied to copy milled bars.

In this manner, the procedure for fabricating and installing a final hybrid takes only two visits to the restorative dentist.

Manufacture of Final Hybrid without Duplicate Temporary Hybrid

In contrast, after osseointegration is complete, five or more visits to the restorative dentist are required to make a final hybrid prosthesis in the immediate load protocol as typically carried out. This protocol is generally described in BIOMET 3I Restorative Manual (CATRM), Flexibility By Design.

In the first visit to the restorative dentist in the immediate load protocol as it is currently carried out, the temporary hybrid is first removed. Then metal devices referred to as impression copings are attached to the implants with screws. These impression copings look similar to the temporary cylinders that are located inside the temporary hybrid. A custom tray is then filled with impression material and placed onto the jaw with the impression copings screwed into the implants. The screws holding the impression copings to the implants are then unscrewed (through access holes in the custom tray), and the custom tray with impression material and impression copings in it is removed. The temporary hybrid is re-attached to the patient's mouth, completing the first visit.

The impression material with the impression copings in it is now given to the dental laboratory. Implant analogs are attached to the impression copings with screws. Soft tissue material is applied to the surface of the impression material that interfaced with the patient's gums. Then the impression material with impression copings, implant analogs and soft tissue material is pressed into a patty of dental stone. After the dental stone hardens, the impression copings and the impression material are removed by unscrewing the screws holding the impression copings onto the implant analogs. This leaves a model of the patient's jaw, with a thin, horse-shaped layer of soft tissue material on the hardened dental stone, with implant analogs protruding from the dental stone through the layer of soft tissue material.

At this point, a set of temporary cylinders is screwed onto the model. A horseshoe-shaped bar of acrylic is used to connect the temporary cylinders to one another. This device—the temporary cylinders connected to one another by a horseshoe-shaped acrylic bar—is commonly referred to as a "verification jig" (or "verification index").

Next, a sheet of acrylic is placed on the model of the jaw being repaired composed of dental stone, implant analogs and soft tissue material. Light is shone on this layer of acrylic to cure it. This layer of acrylic is known as a "base plate." An approximately ½ inch layer of wax in the shape of a horseshoe is then formed on the base plate. This device, composed of the base plate plus the wax horseshoe, may be referred to as a "VDO device" or a "base plate with an occlusal rim." Now it is time for the second visit to the restorative dentist. It takes approximately 2.5 hours of dental laboratory time between the first and second visits to the restorative dentist under the immediate load protocol as currently carried out.

During the second visit, after removing the temporary hybrid, the restorative dentist attaches the verification jig to the implants with screws and checks to see that it fits properly. In this way, the restorative dentist uses the verification jig to verify that the spacing and orientation of the temporary cylinders in the model (which will be used to fabricate the final hybrid) is correct.

Also on the second visit, the VDO device is placed into the mouth like a traditional denture (on the jaw that is being repaired), and the patient bites into the horseshoe-shaped wax material.

Also on the second visit, the restorative dentist will take an impression of the patient's jaw that is not being repaired.

The temporary hybrid is then screwed back into the implants, thus completing the second visit. This visit takes approximately 1.5 hours of "chair time" with the restorative dentist.

After the second visit to the restorative dentist, the dental laboratory uses the impression of the patient's jaw that is not being repaired to make a stone model of that jaw.

The dental laboratory also takes the VDO device (i.e., the base plate with an occusal rim) and places it onto the model of the patient's jaw that is being repaired that was made after the first visit to the restorative dentist. This is the hardened dental stone with the thin layer of horseshoe-shaped soft tissue material on its surface, and with the implant analogs embedded into the stone and protruding through the soft tissue material. Both jaw models are placed into an articulator (including the model of the jaw that is being repaired with the VDO device attached to it), and the VDO device is used to properly set the VDO between the two jaws in the articulator.

Next the wax is removed from the VDO device and a set of denture teeth (or hybrid teeth) is attached to the base plate with wax. Now it is time for the third visit to the restorative dentist. It takes approximately 2 hours of dental laboratory time between the first and second visits to the restorative dentist under the immediate load protocol as currently carried out.

During the third visit, the dentist removes the temporary hybrid, and inserts the base plate with the teeth attached to it with wax. The teeth on the base plate should occlude properly with the opposing set of teeth in the patient's mouth. This step—checking the occlusion using the base plate with teeth attached to it with wax—is commonly referred to as a wax "try in."

The base plate with teeth attached to it with wax is removed from the patient's mouth, and the temporary hybrid is re-attached using screws. This completes the third visit. This visit takes approximately 1 hour of chair time with the restorative dentist.

At this point, the dental laboratory uses the base plate with the teeth attached to it with wax to design a metal bar to be used in the final hybrid using a computer scanner and CAD program as described above. The computer scanner and CAD program can be set to make the teeth and wax be translucent, while the model is opaque, which facilitates the design of a metal bar that will fit within the teeth and wax, and that will mate with the model.

After the metal bar is designed, it is fabricated using a milling machine as described above. Then teeth are attached to the metal bar using wax.

Now it is time for the fourth visit to the restorative dentist. During the fourth visit, the restorative dentist removes the temporary hybrid and checks to make sure that the titanium bar with the teeth attached to it with wax fits properly. The temporary hybrid is re-attached to the patient's mouth with screws, thus completing the fourth visit. This visit takes approximately 1 hour of chair time with the restorative dentist.

The dental laboratory then removes the wax by boiling it out, and replaces the wax with acrylic (as described above). This constitutes the final hybrid. It is cleaned up and polished.

Now it is time for the fifth visit to the restorative dentist. During this visit, the temporary hybrid is removed, and the final hybrid is attached to the patient's mouth with screws. The access holes for the screws are filled in, and the process is complete.

As can be seen, it takes at least five visits to the restorative dentist to fabricate and install a final hybrid after osseointegration using the immediate load protocol as currently carried out (i.e., without using a duplicate temporary hybrid). However, often one or more of the visits must be repeated because the visit reveals that one of the pieces does not fit properly. For example, the verification jig may reveal that the temporary cylinders in the model do not have the proper spacing and orientation, necessitating at least one extra visit. Or the wax "try in" step may reveal that the occlusion is not correct, necessitating at least one extra visit. Thus, it often takes more than five visits to the restorative dentist to fabricate and install a final hybrid after osseointegration using the immediate load protocol as currently carried out.

ADVANTAGES OF THE PRESENT INVENTION

In contrast, as described above, only two visits to the restorative dentist are needed when the duplicate hybrid of the present invention is utilized in making a final hybrid. This is because the duplicate hybrid may serve multiple purposes during the fabrication of the final hybrid. First, the duplicate hybrid may serve the same purpose served by the "custom tray" during the immediate load protocol as currently carried out, which is to hold the impression material that is used to take an impression of the patient's healed gums. Second, the duplicate hybrid may be used to serve the same purpose served by the "verification jig" during the immediate load protocol as currently carried out, which is to verify that the temporary cylinders in the model of the patient's jaw being repaired are in the proper location and orientation. Third, the duplicate temporary hybrid may be used to serve the same purpose as the "VDO device" (i.e., the base plate with an occlusal rim) during the immediate load protocol as currently carried out, which is to ensure that the VDO of the model is correct. Fourth, the duplicate temporary hybrid may be used to ensure that the centric relation of the model is correct. Those skilled in the art will appreciate that the duplicate temporary hybrid may serve other useful purposes. For example, the duplicate temporary hybrid may be installed in the patient's mouth if the original temporary hybrid breaks or becomes damaged in some manner.

In these ways, use of the duplicate temporary hybrid in fabricating the final hybrid saves at least three visits to the restorative dentist, and at least approximately 3.5 hours of "chair time" with the restorative dentist. In particular, the need for the second, third and fourth visits to the restorative dentist under the immediate load protocol as currently carried out is eliminated, saving 3.5 hours of chair time (1.5 hours for the second visit, 1 hour for the third visit and 1 hour for the fourth visit). The duplicate temporary hybrid also saves at least approximately 4.5 hours of dental laboratory time. In particular, the need for the dental laboratory time between the first and second visits (2.5 hours) and between the second and third visits (2 hours) under the immediate load protocol as currently carried out is eliminated. Consequently, the visits to the restorative dentist can occur over a significantly shorter period of time. Specifically, the visits may occur over a period of a few weeks with the duplicate temporary hybrid rather than over a period of several months without the duplicate temporary hybrid.

Moreover, the "extra" visits that are often needed under the immediate load protocol as currently carried out because one of the pieces (such as the verification jig or wax "try in") does not fit properly are avoided with the present invention because such incorrect fits are identified at the dental laboratory, rather than during a visit to the restorative dentist.

Further Applications for the Present Invention

The present invention has been described above in the context of replacing all of a patient's teeth in one jaw ("full arch" tooth replacement). However, the present invention is also applicable in situations where (1) all of the patient's teeth in both jaws are being replaced (replacement of both arches), and (2) a patient is having less than all of the teeth in one jaw or less than all of the teeth in both jaws replaced. The present invention has also been described above in the context of the immediate load protocol (i.e., in a situation where a patient receives a temporary hybrid at the time of the surgical visit where the dental implants are implanted). However, the present invention is applicable whenever a patient receives a temporary hybrid prosthesis and then later receives a final hybrid prosthesis. For example, the present invention would be applicable where a patient does not receive a temporary hybrid during the surgical visit when dental implants are implanted (because, for example, the patient is not eligible for the immediate load protocol), but rather receives a temporary denture at that time (which is not attached to the implants but rather is fastened to the mouth like a traditional denture), and then receives a temporary hybrid after osseointegration is complete, followed later by a final hybrid. A temporary hybrid might be used in these circumstances because the patient is dissatisfied with having to wear a temporary denture for any longer than is necessary, since the temporary denture is not as tightly attached to the patient's mouth as a temporary hybrid (which is screwed onto the implants).

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A method of making a final hybrid prosthesis to be attached to one or more dental implants in a patient's mouth, comprising:

making a temporary hybrid prosthesis to be attached to the one or more dental implants in the patient's mouth, wherein the temporary hybrid prosthesis comprises a first set of tooth-shaped structures made out of a first tooth-forming material and a first set of cylinders, wherein the first set of tooth-shaped structures and the first set of cylinders are connected together with a first mass of material, and wherein the temporary hybrid prosthesis is configured to be attached to the one or more dental implants in the patient's mouth;

making a duplicate temporary hybrid prosthesis from the temporary hybrid prosthesis, wherein the duplicate temporary hybrid prosthesis has the same size and shape as the temporary hybrid prosthesis, wherein the duplicate temporary hybrid prosthesis comprises a second set of tooth-shaped structures made out of a second tooth-forming material and a second set of cylinders, wherein the second set of tooth-shaped structures and the second set of cylinders are connected together with a second mass of material, and wherein the duplicate temporary hybrid prosthesis is configured to be attached to the same one or more dental implants in the patient's mouth to which the temporary hybrid prosthesis is configured to be attached; and using the duplicate temporary hybrid prosthesis in making the final hybrid prosthesis while the temporary hybrid prosthesis is attached to the one or more dental implants in the patient's mouth, wherein the final hybrid prosthesis comprises a third set of tooth-shaped structures made out of a third tooth-forming material and a third set of cylinders, wherein the third set of tooth-shaped structures and the third set of cylinders are connected together with a third mass of material, wherein the third set of cylinders are connected together by a bar enclosed within the third mass of material, and wherein the final hybrid prosthesis is configured to be attached to the same one or more dental implants in the patient's mouth to which the temporary hybrid prosthesis is configured to be attached.

2. The method according to claim 1, wherein the temporary hybrid prosthesis to be attached to the one or more dental implants in the patient's mouth and the duplicate temporary hybrid prosthesis are made during or after a dental visit when the one or more dental implants are implanted.

3. The method according to claim 1, wherein the temporary hybrid prosthesis is made from a denture previously worn by the patient.

4. The method according to claim 1, wherein the duplicate temporary hybrid prosthesis is made during a dental visit when the one or more dental implants are implanted.

5. The method according to claim 1, wherein, in response to the duplicate temporary hybrid prosthesis being made during a dental visit when the one or more dental implants are implanted, no more than two visits to a restorative dentist thereafter are needed to make and install the final hybrid prosthesis.

6. The method according to claim 1, wherein, in response to the duplicate temporary hybrid prosthesis being made during a first visit to a restorative dentist after a dental visit when the one or more dental implants are implanted, exactly one visit to a restorative dentist thereafter is needed to make and install the final hybrid prosthesis.

7. The method according to claim 1, wherein the first set of tooth-shaped structures of the temporary hybrid prosthesis to be attached to the one or more dental implants in a patient's mouth includes tooth-shaped structures for at least one of a patient's entire upper jaw or entire lower jaw.

8. The method according to claim 1, wherein the third set of tooth-shaped structures of the final hybrid prosthesis includes tooth-shaped structures for at least one of a patient's entire upper jaw or entire lower jaw.

9. The method according to claim 1, wherein the using the duplicate temporary hybrid prosthesis in making the final hybrid prosthesis includes scanning the duplicate temporary hybrid prosthesis.

10. The method according to claim 1, wherein the making of the duplicate hybrid prosthesis from the temporary hybrid prosthesis includes scanning the temporary hybrid prosthesis.

11. The method according to claim 1, wherein the first tooth-forming material and the second tooth-forming material are different materials.

12. A method comprising (i) making a duplicate temporary hybrid prosthesis from a temporary hybrid prosthesis wherein the temporary hybrid prosthesis comprises a first set of tooth-shaped structures made out of a first tooth-forming material and a first set of cylinders, wherein the first set of tooth-shaped structures and the first set of cylinders are connected together with a first mass of material, and wherein the temporary hybrid prosthesis is configured to be attached to one or more dental implants in the patient's mouth, and wherein the duplicate temporary hybrid prosthesis has the same size and shape as the temporary hybrid prosthesis, wherein the duplicate temporary hybrid prosthesis comprises a second set of tooth-shaped structures made out of a second tooth-forming material and a second set of cylinders, wherein the second set of tooth-shaped structures and the second set of cylinders are held together with a second mass of material, and wherein the duplicate temporary hybrid prosthesis is configured to be attached to the same one or more dental implants in the patient's mouth to which the temporary hybrid prosthesis is configured to be attached, and (ii) using the duplicate temporary hybrid prosthesis in making a final hybrid prosthesis while the temporary hybrid prosthesis is attached to the one or more dental implants in a patient's mouth, wherein the final hybrid prosthesis comprises a third set of tooth-shaped structures made out of a third tooth-forming material and a third set of cylinders connected together with a third mass of material, wherein the third set of cylinders are connected together with a bar enclosed within the third mass of material, and wherein the final hybrid prosthesis is configured to be attached to the same one or more dental implants in the patient's mouth to which the temporary hybrid prosthesis is configured to be attached.

13. The method according to claim 12, wherein the temporary hybrid prosthesis is made from a denture previously worn by the patient.

14. The method according to claim 12, wherein the using the duplicate temporary hybrid prosthesis in making the final hybrid prosthesis includes scanning the duplicate temporary hybrid prosthesis.

15. The method according to claim 12, wherein the making of the duplicate hybrid prosthesis from the temporary hybrid prosthesis includes scanning the temporary hybrid prosthesis.

16. The method according to claim 12, wherein the first tooth-forming material and the second tooth-forming material are different materials.

\* \* \* \* \*